（12）United States Patent
Hooker et al.

(10) Patent No.: US 6,554,463 B2
(45) Date of Patent: Apr. 29, 2003

(54) OPTICAL WAVEGUIDE CONCENTRATOR AND ILLUMINATING DEVICE

(75) Inventors: Brian Hooker, Boulder, CO (US); Joshua Friedman, Ridgefield, CT (US)

(73) Assignee: AdDent Inc., Danbury, CT (US)

( * ) Notice: Subject to any disclaimer, the term of this patent is extended or adjusted under 35 U.S.C. 154(b) by 0 days.

(21) Appl. No.: 09/923,065

(22) Filed: Aug. 6, 2001

(65) Prior Publication Data

US 2002/0051367 A1 May 2, 2002

Related U.S. Application Data

(63) Continuation-in-part of application No. 09/574,444, filed on May 19, 2000.

(51) Int. Cl.[7] .................................................. F21V 8/00
(52) U.S. Cl. ...................... 362/555; 362/800; 362/242
(58) Field of Search ................................. 362/555, 800, 362/578, 577, 579, 242, 30, 27, 26; 358/509, 505, 512

(56) References Cited

U.S. PATENT DOCUMENTS

| 5,420,768 A | * | 5/1995 | Kennedy | 362/119 |
| 5,634,711 A | * | 6/1997 | Kennedy | 362/119 |
| 6,191,872 B1 | * | 2/2001 | DeCaro | 358/509 |

* cited by examiner

Primary Examiner—Thomas M. Sember
Assistant Examiner—Hargobind S. Sawhney

(57) ABSTRACT

An optical waveguide concentrator and photocuring device with the optical waveguide concentrator having at least one solid optically transparent member for combining the output radiant energy from a plurality of optoelectronic light emitting devices mounted in a circular array facing the solid optically transparent member with the optically transparent member having an input surface, an output surface and a sloping surface intersecting the input and output surface to form an acute angle and with with each optoelectronic light emitting device having an optical axis directed parallel to or inclined relative to the longitudinal axis of the concentrator. The geometry of the solid optically transparent member may be conical or hyperbolic with the sloping surface tapered to form a tapered angle of between 5° and 15°.

21 Claims, 7 Drawing Sheets

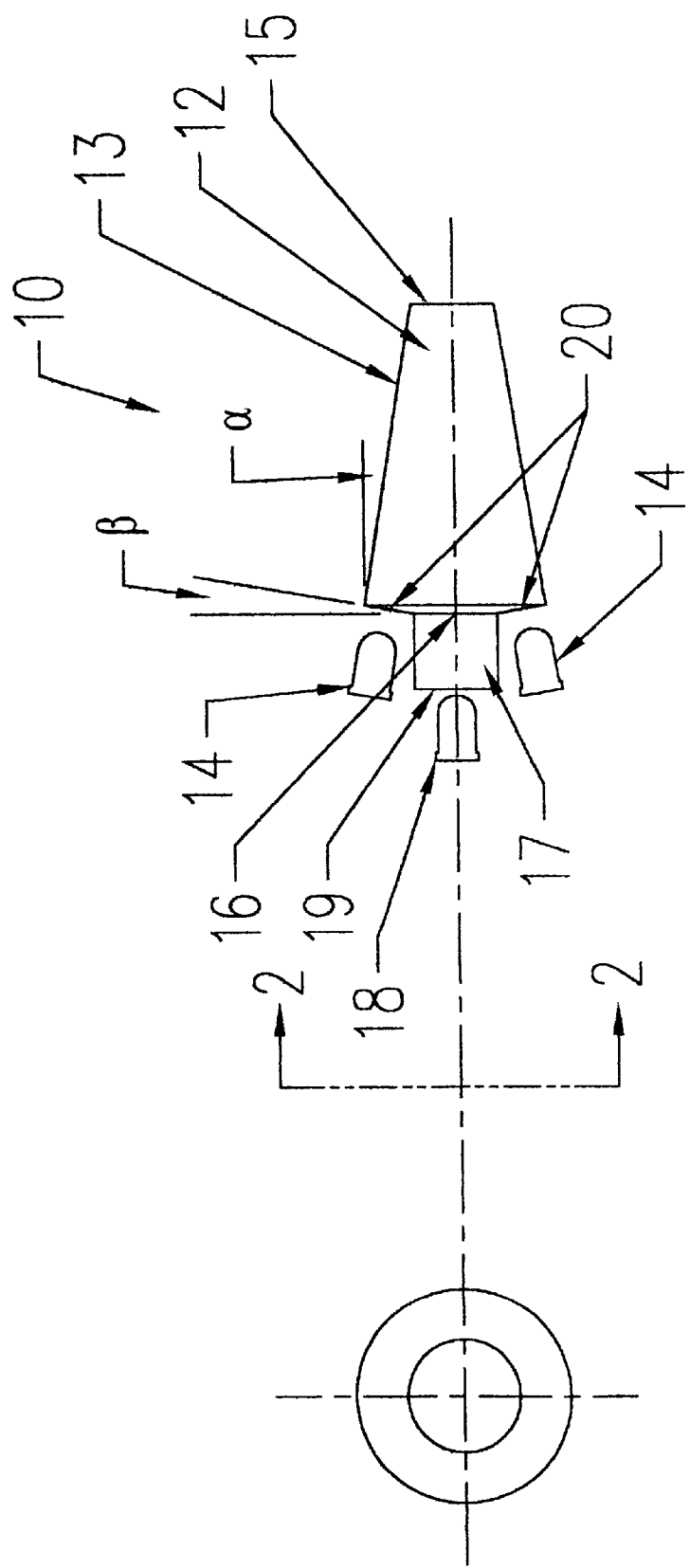

US 6,554,463 B2

OPTICAL WAVEGUIDE CONCENTRATOR AND ILLUMINATING DEVICE

FIELD OF THE INVENTION

This invention is a continuation-in-part of U.S. patent application Ser. No. 09/574,444 filed May 19, 2000 and relates to an optical waveguide concentrator for combining the output radiant energy from an array of optoelectronic light emitting devices and to a combination illuminating device and optical waveguide concentrator for producing controlled output levels of radiant energy for curing polymerizing materials in various industrial, medical and dental fields of applications.

BACKGROUND OF INVENTION

Light emitting illuminating devices are currently used in many different technical fields to photochemically cure light activated materials. For example, in the medical field, photodynamic therapy drugs, such as psoralens and hematoporhorins, are currently being prescribed to induce a chemical reaction upon the application of radiant energy in the 600–700 nanometer range. In the field of dentistry it is now conventional to use light emitting illuminating devices to cure dental restorative materials, in situ, within a patients mouth, as well as in the dental laboratory. Numerous commercial applications also exist where adhesives and coatings use light activated materials which are photochemically cured by application of a light emitting illuminating device.

In a conventional photocuring device a gas filled lamp such as a mercury vapor, metal halide, florescent, halogen lamp or laser is used as the light source to generate radiant energy. The traditional gas pressure discharge and halogen lamp causes the photocuring device to generate a substantial amount of heat during operation and therefor requires an adequate heat dissipating system. Accordingly, such devices are large and complex. Moreover, in the case of gas pressure discharge lamps and lasers, long fiberoptic bundles are needed to transmit light from the source to the point of application. These bundles are costly and prone to break.

Although optoelectronic semiconductor and solid state light emitting devices including solid state lasers are commercially available, the radiant energy output from a single one of such devices is much too low to be useful as a light source for use in a photocuring device particularly when compared to the radiant output energy of, for example, a conventional halogen lamp. However, if the output radiant energy from a multiple number of conventional solid state light emitting devices were to be combined in an efficient manner, the total optical power generated would be theoretically sufficient to cure light activated materials in many industrial, medical and dental applications. A portable photocuring device which is directed to the concept of combining a multiple array of solid state LED's to produce a combined source of light for use in a photocuring device is taught in U.S. Pat. No. 5,420,776 and U.S. Pat. No. 5,634, 711 respectively. The light output from the array of LED's is transmitted through an optical light guide and condensed to form a single output beam of light in a fiber optic conduit. The arrangement taught in these patents does not adequately combine the output radiant energy from the LED's without substantial loss of energy. This loss necessitates a larger number of solid state LED's to produce an adequate output of light energy. The number of solid state LED's which may be used is limited for a hand held device and increases the difficulty in handling the heat generated in a concentrated small area by a large number of closely packed LED's. In some applications there may not even be sufficient space to package the required number of LED'S to provide adequate curing.

SUMMARY OF THE INVENTION

The present invention is directed to an optical waveguide concentrator for combining the output radiant energy from a plurality of optoelectronic light emitting devices with minimal loss of radiant energy to the surrounding atmosphere. The present invention is also directed to a light emitting photocuring device for use in combination with the optical waveguide concentrator for providing a controlled optical output from an array of individual solid state light emitting devices wherein the total light energy output is equal to the cumulative addition of the output radiant energy from each of the individual solid state light devices with minimal energy lost to the surrounding atmosphere. For purposes of the present invention an optoelectronic light emitting device may represent a single light source of any known type but preferably selected from the group consisting of solid state or semiconductor light emitting diode(s) i.e., "LED's", light emitting polymers and semiconductor lasers. In accordance with the present invention the LED'S may have different wave length outputs which can be selectively turned on or off. For example the illuminating device of the present invention may have diodes with a 360 nm wave length output as well diodes with a 470 nm wave length output. This configuration could be used to cure materials in the 300–400 nm range as well as materials in the 400–500 nm range.

The optical waveguide concentrator of the present invention comprises at least one solid optically transparent member having an input surface, an output surface, a sloping surface intersecting the input and output surface to form an acute angle thereto, and a plurality of optoelectronic light emitting devices mounted in a substantially circular array facing said input surface with each optoelectronic light emitting device having an optical axis directed to intersect the longitudinal axis of the concentrator. In the preferred embodiment the input surface can be either flat or convex, the sloping surface can be conical or hyperbolic and the output or exit surface can be flat or concave depending upon the selection of the sloping surface. The sloping surface should have a taper such that the acute angle, in cross section, lies between 5° and 15° with respect to a plane parallel to the longitudinal axis of the concentrator.

The photocuring device of the present invention comprises a housing having a longitudinal axis, a waveguide concentrator having at least one solid optically transparent member of frustoconical geometry aligned with its longitudinal axis concentric to the longitudinal axis of the housing and having, in cross section, a sloping surface with a tapered angle of between 5° and 30°, an input and an output surface substantially intersecting the sloping surface, an array of optoelectronic light emitting devices mounted to face said input surface with the optical axis of each light emitting device directed to intersect the longitiudinal axis of the concentrator, a source of power for said array of optoelectronic light emitting devices, control means for controlling the output from said waveguide concentrator and a light guide having one section internal of said housing in alignment with said longitudinal axis and in physical proximity to said waveguide concentrator and a curved section extending from said housing external of said photocuring device. The waveguide concentrator may have a further inclined surface extending from the input surface to the conical surface in a plane lying at an angle to the plane of the input surface substantially equal to said tapered angle ±50% for mounting said array of optoelectronic light emitting devices with the optical axis of each optoelectronic light emitting device lying substantially perpendicular to said inclined surface.

BRIEF DESCRIPTION OF THE DRAWINGS

Other features and advantages of the present invention will become apparent from the following detailed description of the invention when read in conjunction with the accompanying drawings of which:

FIG. 1 is a cross sectional diagrammatic view of a one stage optical waveguide concentrator of the present invention having a single optical transparent member and a plurality of optoelectronic light emitting devices;

FIG. 2 is a side view of FIG. 1 taken along the lines 2—2 of FIG. 1;

DETAILED DESCRIPTION OF THE PREFERRED EMBODIMENT

Figure 3:
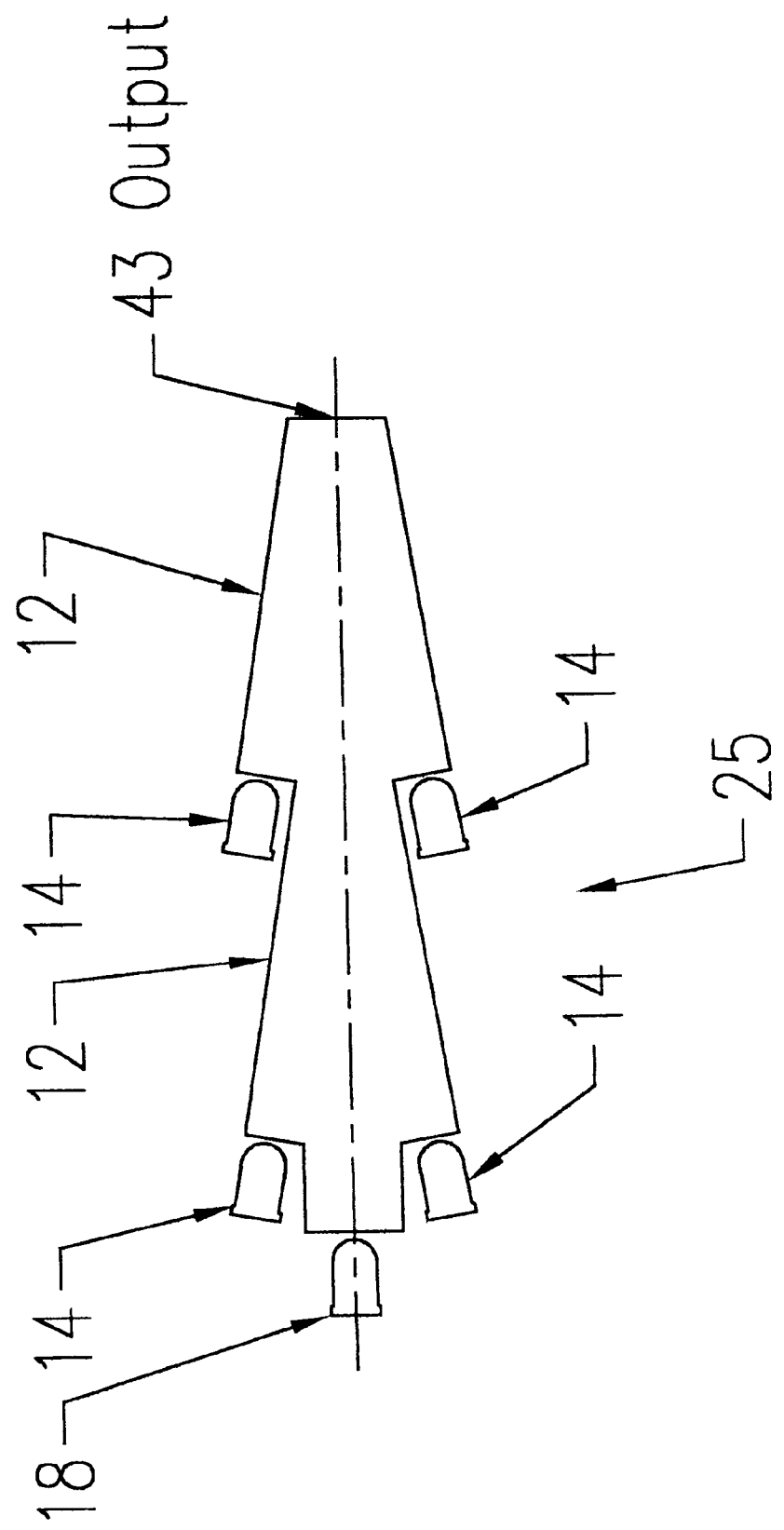
FIG. 3 is a cross sectional view of a two stage optical waveguide concentrator of the present invention having two optical transparent members arranged in tandem and a multiple number of optoelectronic light emitting devices.

The present invention is best understood with reference to FIGS. 1 and 2 in which the waveguide concentrator 10 of the present invention is limited to a single stage including an optical transparent member 12 and a plurality of optoelectronic light emitting devices 14 arranged around the optical transparent member 12. The geometry of the optical transparent member 12 and the arrangement of the light emitting devices 14 confine the light radiated by each of the optoelectronic light emitting devices 14 to internal reflections within the waveguide concentrator 10 so that essentially no radiant energy is lost to the surrounding atmosphere.

The optical transparent member 12 is composed of an optically clear material of high transmittivity selected from the group consisting of glass, quartz or of any transparent plastic such as acrylic or polycarbonate. In addition, the composition of the optical transparent member 12 must have an index of refraction greater than the surrounding atmosphere (air). Alternatively, the optical transparent member 12 may be coated with a metal or dielectric reflector to reflect and contain light so as to inhibit light rays from escaping through the walls of the optical transparent member 12. An example of an optical transparent member 12 of commercially available plexiglass would have an index of refraction at 470 nm of 1.49 and an external transmittance at 470 nm of 0.92. Accordingly, one can predict a loss due to absorption in a rod of plexiglass having a diameter of 11 mm of only 0.5% per 3 mm thickness.

The optical transparent member 12 should have a frusto-conical geometry which in cross section, as shown in FIG. 1, forms a conical surface 13 having a predetermined tapered angle $\alpha$ with respect to a plane parallel to the longitudinal axis of the transparent member 12. The optical transparent member 12 should also have an essentially flat end face 15 and an input surface 16 defining the output and input surfaces respectively of this single stage waveguide concentrator. The end face 15 and the input surface 16 should lie substantially transverse to the longitudinal axis of the optical transparent member 12. An optional cylindrical section 17 may be included as part of the waveguide concentrator 10 to facilitate mounting of the optoelectronic light emitting devices 14 and to provide for the mounting of additional light emitting devices 18 aligned coaxial with the longitudinal axis. The cylindrical section 17 should be transparent and of the same composition as that of the member 12 and should extend from the input surface 16 concentric to the longitudinal axis of the member 12.

The optical transparent member 12 must also have an inclined surface 20 which extends from the input surface 16 to the conical surface 13 and lies in a plane at an angle $\beta$ to the plane of the input surface as shown in FIG. 1. This inclined surface 20 defines a tapered window region for coupling light from the plurality of optoelectronic light emitting device 14 into the waveguide concentrator 10. The plurality of the optoelectronic light emitting devices 14 are mounted about the optical transparent member 12 with the optical axis of each intersecting the inclined surface 20. The number of optoelectronic light emitting devices 14 which can be mounted facing the inclined surface 20 is dependent upon the physical size of each optoelectronic light emitting device 14 and the physical size of the optical transparent member 12. It is not essential to the present invention that the optoelectronic light emitting devices be of the same type or generate light in the same wavelength region. Instead the optoelectronic devices may intentionally be selected to generate different wavelengths depending upon the application of the waveguide concentrator 10. When optoelectronic light emitting devices 14 are used having different wavelengths it is preferable to also use switch means to selectively turn the light emitting devices of different wavelengths on and off. Any conventional switch type means may be used to perform this on and off switch function and preferably under the control of the operator.

One or more additional optoelectronic light emitting devices 18 may also be arranged with their optical axes in alignment with the longitudinal axis of the optical transparent member 12. These optoelectronic light emitting devices 18 are preferably of the same type as the optoelectronic light emitting devices 14 although they need not be and can also be of different wavelength. If the cylindrical section 17 is not present the optoelectronic device 18 would direct light into the input face 16 whereas if the cylindrical section 17 is included the optoelectronic device 18 would direct light into the input face 19. Once light is inside the waveguide concentrator 10 each light ray incident on the conical surface 13 will be entirely reflected unless the angle of incidence at the conical surface 13 is less than the "critical angle" of incidence of the transparent member 12. The reflected rays of light will continue to be reflected from the conical surface 13 until exiting the output face 15 of the concentrator 10 as a concentrated single beam of light. The taper angles "α" and "β" are critical to the present invention. The taper angle "α" will determine the number of reflections within the single stage waveguide concentrator 10 for a given length of the transparent member 12. With each reflection the angle of incidence on the surface 13 increases until the rays exceed the critical angle and are no longer internally reflected. Accordingly, the preferred taper angle "α" should preferably be about 10°±50%, i.e., between about 50° and 15°. The taper angle "β" maximizes the coupling of light into the waveguide concentrator from the annular array of optoelectronic light emitting devices 14 facing the inclined surface 20. Assuming that the light from each optoelectronic light emitting device 14 emits light in a cone having an emitting divergence of no more than about 15 degrees the taper angle "β" should then also be about 10°±50% and preferably equal to said taper angle "α". The taper angle "α" controls the number of reflections in the transparent member 12. It is preferred to limit the number of reflections to a minimum number. For a given waveguide concentrator 10 with an overall length of no more than 90 mm and using an array of optoelectronic devices 14 having a cone shaped divergence of no more than about 15 degrees the total number of reflections can be limited to two. If the divergence of the beam from the optoelectronic devices 14 is less than 15 degrees many more reflections are possible before any light will begin to leak out of the waveguide concentrator 10. It should be understood that in the present invention any optoelectronic light emitting device 14 may be used with a beam divergence of no more than about 15 degrees. However, the radiation pattern of the light may vary. Examples of different suitable sources of light include a helium-neon laser, diode laser and solid state LED.

Figure 5:
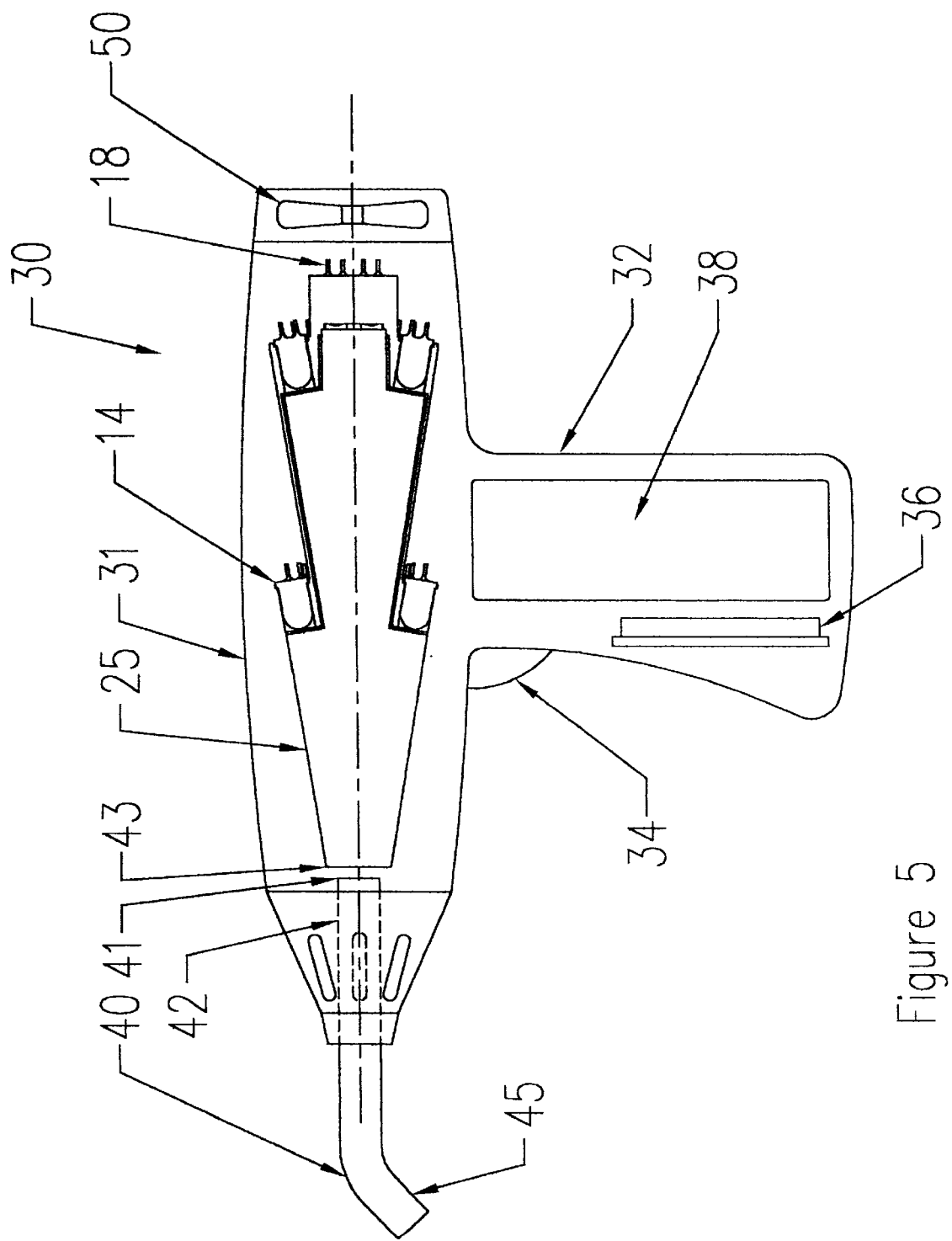
FIG. 5 is a diagrammatic view in cross section of a combined embodiment of the light emitting illuminating device and optical waveguide concentrator of the present invention with many of the components identified in block diagram format.

The waveguide concentrator 10 of the present invention may consist of more than one stage i.e., it may include a plurality of successive stages having a plurality of optical transparent members 12 arranged in tandem. A preferred two stage waveguide concentrator 25 is shown in FIG. 3. The geometric characteristics of each optical transparent member 12 should be substantially the same in the multi-stage waveguide concentrator 25 of FIG. 3 relative to the single stage waveguide concentrator 10 of FIG. 1. The use of a second stage permits the inclusion of essentially twice the number of optoelectronic light emitting devices 14. Accordingly, if 10 optoelectronic LED's are mounted in an annular array facing the inclined surface 20 in the one stage waveguide concentrator 10 then 20 optoelectronic LED's may be mounted in the two stage waveguide concentrator 25 of FIG. 3. An additional four optoelectronic LED's 18 may be mounted axially along the longitudinal axis of the optical transparent member 12 at the end opposite the output surface 43 of the waveguide concentrator 25 as shown in FIG. 5. However, there is a diminishing contribution from successive stages in a waveguide concentrator having too many stages. In accordance with the present invention a waveguide concentrator 25 with two tapered sections can provide nearly lossless transmission whereupon the addition of further stages will begin to introduce losses due to the increase in the number of reflections of light rays incident on the conical wall surface 13 in each preceding stage. Accordingly, it is preferred that the number of stages be limited to no more than four based on the size of the waveguide concentrator, the application and the selection of optoelectronic light emitting devices 14, with two stages considered optimal for a hand held photocuring device of about 5 inches in length as shown in FIG. 5 or 6 using conventional LED's as the light emitting devices 14 and 18.

Figure 4:
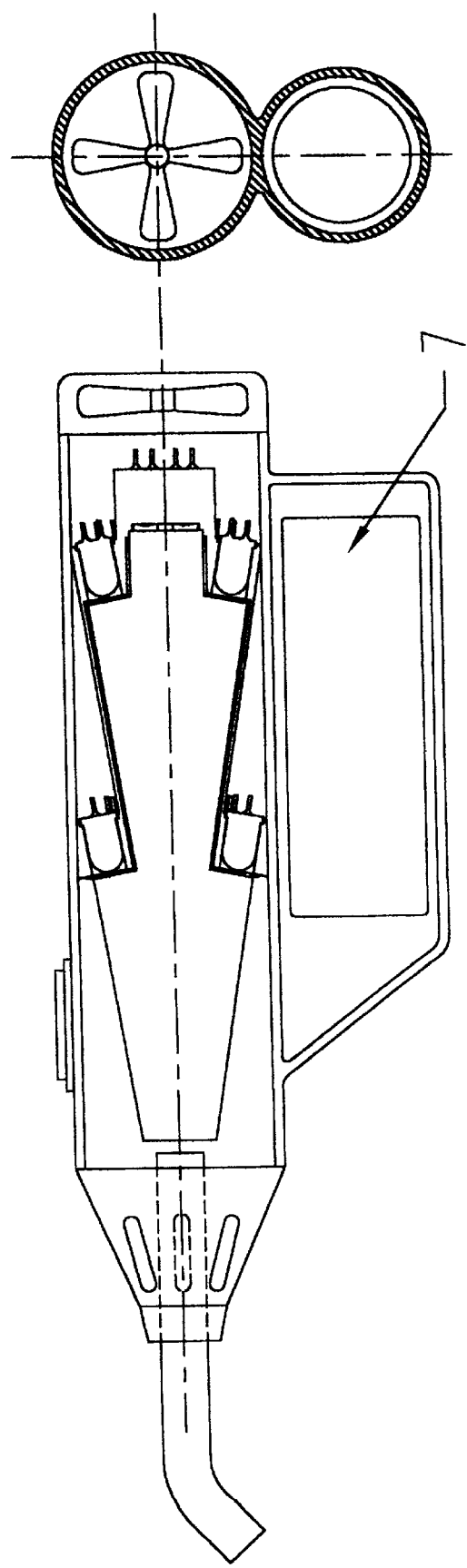
FIG. 4 is a perspective view of a waveguide concentrator and LED holder in a molded configuration to facilitate mounting an array of solid state LED optoelectronic light emitting devices in accurate common alignment about the optical transparent member of the waveguide concentrator.

An arrangement which facilitates mounting a plurality of solid state LED's in the waveguide concentrator 10 or 25 in the form of a circular array about each transparent member 12 is shown in FIG. 4. In the arrangement of FIG. 4 a purality of LED's 18 are also readily inside the cylindrical section 17. The optical transparent member 12 and the cylindrical section 17 is molded in one piece (only one half of which is shown in FIG. 4) to provide multiple openings 27 each of which can receive one LED 14 (not shown) of a given type and size. The openings 27 permit an optimum number of such LED's to be readily mounted in proper alignment so that the optical axis of each such LED will face the inclined surface 20 to intersect it at a right angle. The openings 27 in the cylindrical section 17 provide for the insertion of LED's 18 in alignment with the longitudinal axis of the optical transparent member 12. The two stage configuration of FIG. 4 is designed to mount a total of 24 LED's.

FIG. 5 shows a hand held photocuring device 30 including a two stage waveguide concentrator 25 identical to the concentrator 25 shown in FIG. 3. The photocuring device 30 comprises a housing 31, preferably of plastic, in which the waveguide concentrator 25 is mounted with its longitudinal axis concentric with the longitudinal axis of the housing 31. The waveguide concentrator 25 includes 24 LED's 14 using the arrangement shown in FIG. 4. The housing 31 includes a depending section 32 supporting a trigger push button type actuator 34 which externally extends from the section 32 of the housing 31 for manually actuating or deactivating the operation of the photocuring device 30 and a unit 36 which can be a conventional microprocessor based timing and control circuit for a power source 38 such as a battery or power supply. Alternatively the unit 36 can be a multiconductor power cord for connection to an external power supply and microprocessor based timing and control circuit (not shown). The microprocessor based timing and control circuit 36 functions to control the time and intensity of the output from the photocuring device 30 by controlling the input power and duty cycle of the power supplied to the waveguide concentrator 25. The power source 38 is electrically connected to the unit 36 which in turn is connected through conductors (not shown) to each of the LED's 14 and 18 respectively. A conventional light guide 40 of glass or plastic extends through an opening 41 in the housing 31 of the photocuring device 30. The light guide 40 has a straight section 42 in alignment with the longitudinal axis of the waveguide concentrator 25 and has one end 41 in physical proximity to the output face 43 of the waveguide concentrator 25 and a curved section 45 extending external of the housing 31. The photocuring device 30 may also have a cooling fan 50 which is also connected to the power source 38 by wires (not shown).

Figure 6:
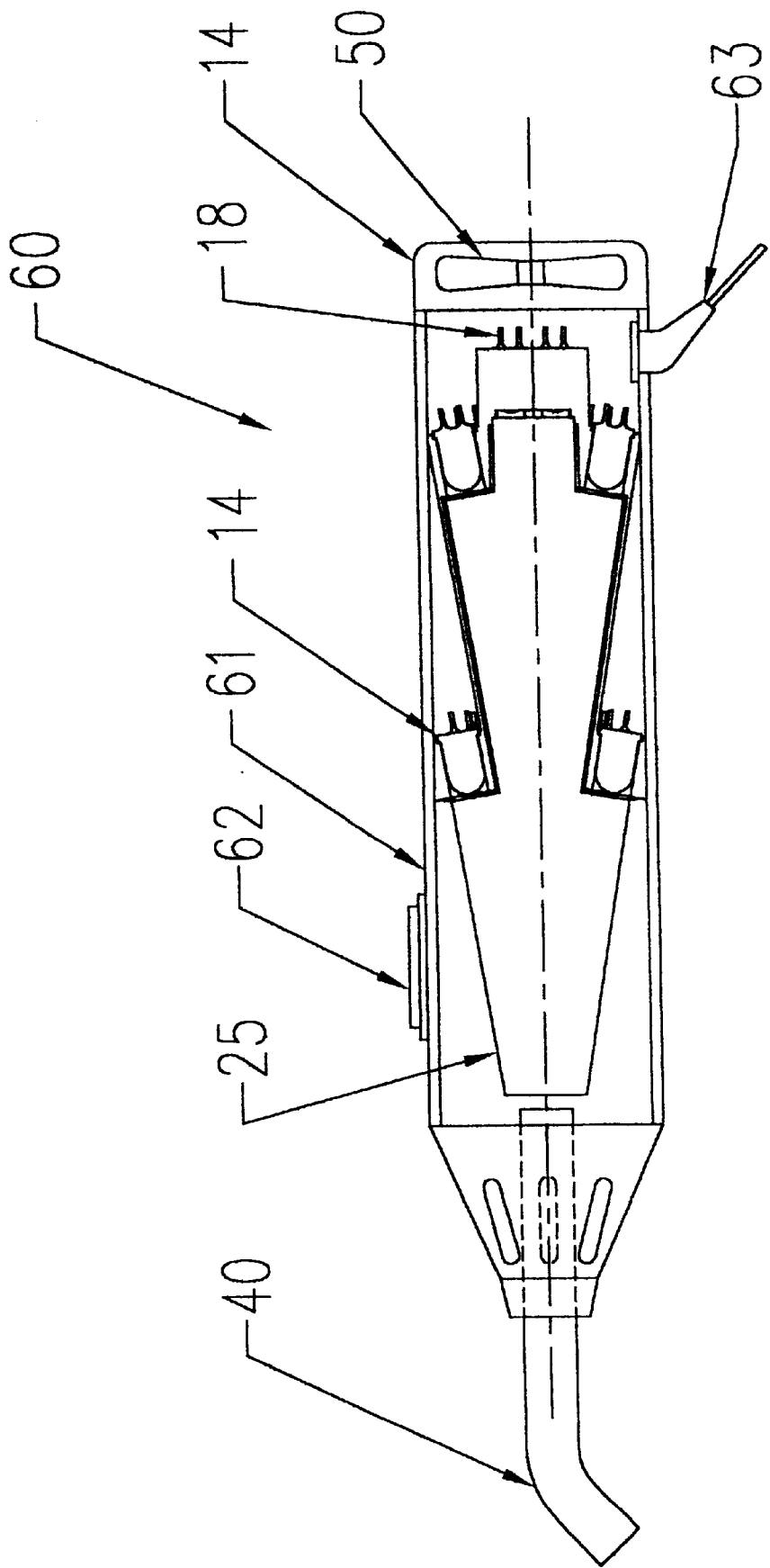
FIG. 6 is a diagrammatic view in cross section of another embodiment for the combined light emitting illuminating device and optical waveguide concentrator of the present invention.

Another embodiment of a hand held illuminating device 60 similar to the device 30 is shown in FIG. 6 using the same reference numbers corresponding to the identical components in FIG. 5. It should be understood that the hand held illuminating device 60 can also be used as a flashlight and can be of one or more stages. In FIG. 6 the waveguide concentrator 25 is a two stage concentrator which is mounted in the device 60 in alignment with the longitudinal axis of its housing 61. A push button 62 mounted on the top surface of the housing 61 is a manual switch for actuating the device. The LED's 14 in the two stage waveguide concentrator 25 can be ultraviolet, blue, green or infrared or a combination thereof. A flexible cord 63 is a multiconductor power cord that extends to an external power supply (not shown) which also contains a microprocessor based timer and control circuit for controlling the time and intensity functions of the device.

Figure 7:
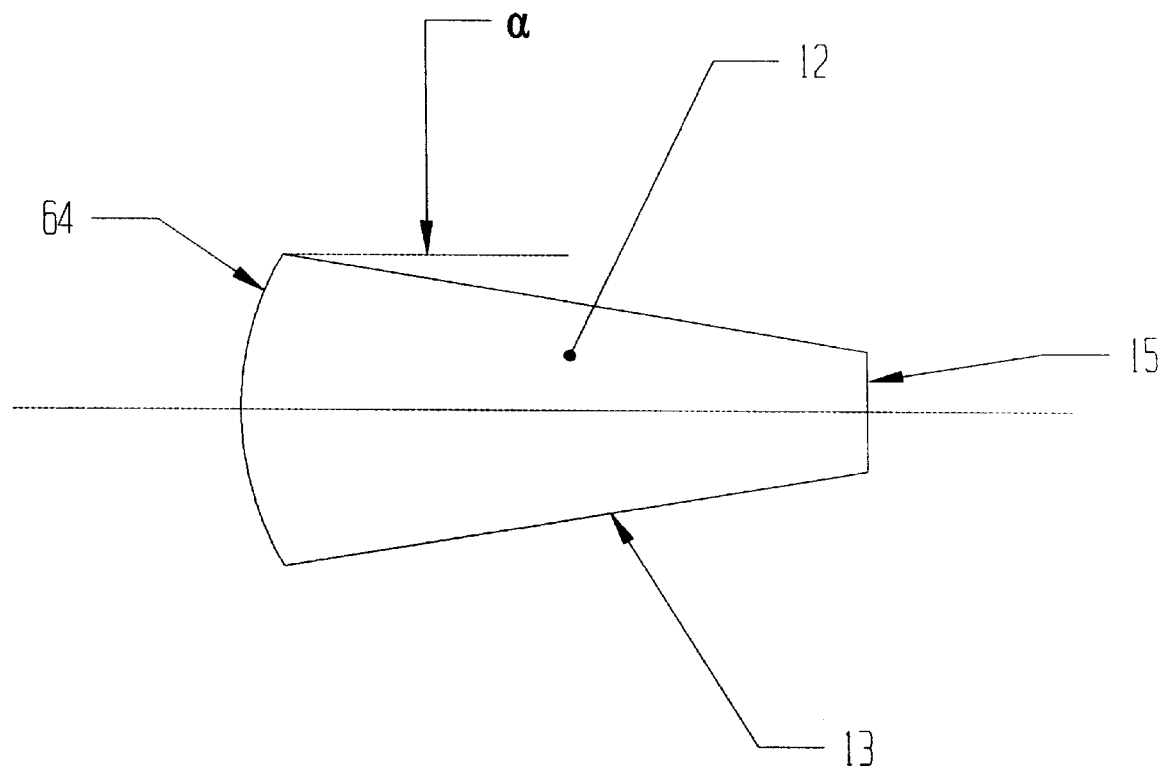
FIG. 7 is a cross sectional view of another embodiment of the solid optical transparent member of FIG. 1 with an input surface of modified geometry.
Figure 8:
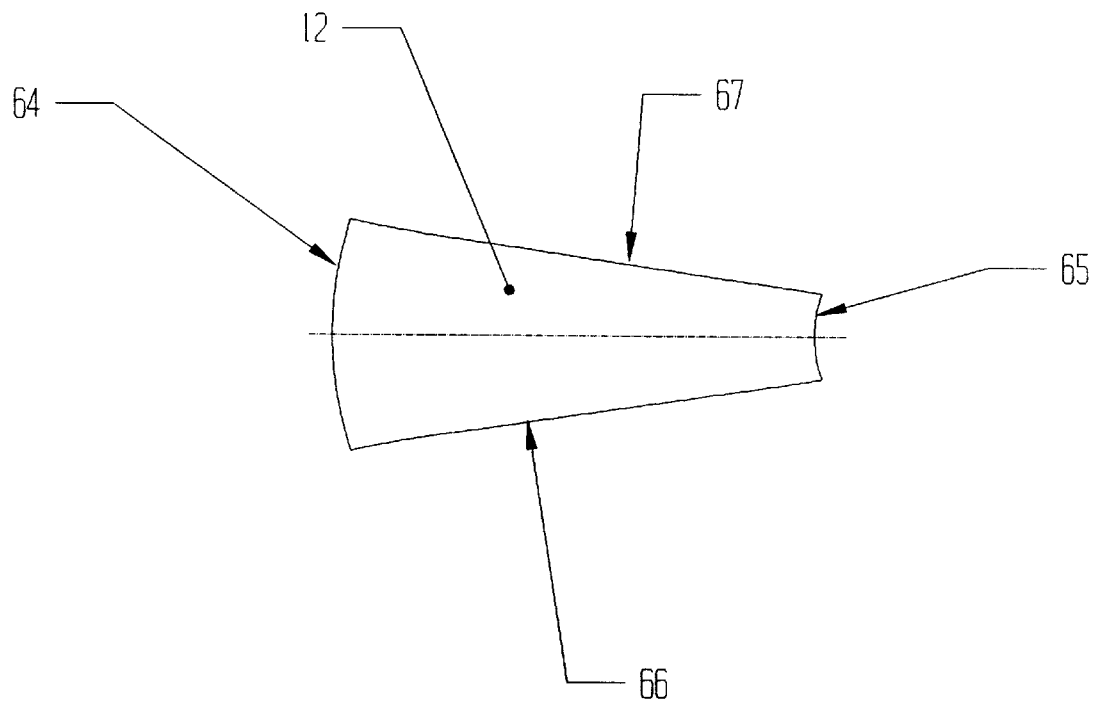
FIG. 8 is a cross sectional view of yet another embodiment of the solid optical transparent member of FIG. 1 having a surface geometry with a sloping surface of hyperbolic curvature.

The design of the optical transparent member 12 of FIG. 1 may be modified as shown in FIGS. 7 and 8 to concentrate light from the array of light emitting diode's 18 (not shown in FIGS. 7 & 8) such that the light will bounce less as it travels through the member 12 before reaching the output surface thereby minimizing the loss in light energy through the optical transparent member 12 and causing the light energy to be more confined at the exit surface, i.e., funnelling the light into a smaller area at the output surface. In this design all of the LED'S may be mounted parallel to the long axis of the waveguide at the input. Concentrating the light at the exit surface to within a smaller area will also maximize the amount of light transferred into a light transmitting medium such as a fiber optic bundle (not shown) which may be readily mounted adjacent the output surface of the optical transparent member 12.

In the embodiment of the optical transparent member 12 shown in FIG. 7 the input surface 64 is curved as opposed to the configuration of the input surface 16 of FIG. 1 which is flat. The curved input surface 64 is preferably convex. For purposes of simplicity the same reference numerals are used for all of the other features which are otherwise in common with the optical transparent member 12 of FIG. 1, i.e., the optical transparent member 12 has a conical surface geometry identical to that of FIG. 1 and a flat output exit surface 15. The use of a convex input surface 64 serves to bend light toward the longitudinal axis of the concentrator.

Another alternative design for the optical transparent member 12 is shown in FIG. 8 which has a curved input surface 64 similar to that of FIG. 7, a curved output surface 65 and an outer surface geometry which, in cross section, takes the form of a hyperboloid having hyperbolic surfaces 66 and 67 respectively. The sloping surfaces 66, 67 intersect the input and output surfaces 64 and 65 to form an acute angle "α" with respect to a plane parallel to the longitudinal axis of the transparent member 12 similar to that formed in the configuration of FIG. 1. The acute angle "α" is preferably in the same range of between 5° and 15° as in the configuration of FIG. 1 which has a frustoconical cross sectional geometry.

The modification of the optical transparent member 12 as shown in both embodiments of FIG. 7 or 8 are intended to reduce the number of internal reflections made by the light rays before exiting the optical transparent member 12 and to provide more control of the angular spread of light at the exit surface. It is recognized that the light traveling down an optical transparent member 12 in a waveguide concentrator 10 or 25 needs to make a minimum number of bounces since at every bounce the angle of incidence to the next surface decreases, which would lead to the following three problems: (1) exiting the concentrator 10 or 25 at too steep an angle to stay away within the acceptable angle of the fiber bundle, (2) the potential for light to reverse itself and return to the source, and (3) not meeting the TIR (Total Internal Reflectance) condition since the incidence angle would be beyond the critical angle. To minimize the number of bounces, a curved input face 64 which is preferably convex in curvature is used to bend light toward the optical axis of the concentrator i.e. its longitudinal axis. The bending of the light rays before they enter the optical transparent member 12 of the concentrator avoids causing reflections until reaching a considerable way down the length of the member 12. Therefore, a typical ray can escape hitting several surfaces before reaching the exit surface keeping the exit angle small and reducing the risk of a back-reflection.

The design of the walls of the optical transparent member 12 for either a single stage or multiple concentrator 10 or 25 based upon the embodiments of FIG. 7 or 8 will have a curved input surface 64 which is preferably convex in curvature with a gently sloping outer surface which forms an hyperboloid or a cone. The hyperbolic surfaces 67 and 68, in cross section, serve to minimize internal reflections and should be configured to be steeper toward the input side 64 and to resemble a cone toward exit side. When a hyperbolic surface geometry is selected for the surface geometry of the optical transparent member 12 the output surface 65 should preferably be curved and more preferably concave to limit the exit angle.

A fiber optic bundle (not shown) would contact the the exit surface 15 or 65 of the optical transparent member 12 in the waveguide concentrator 10 or 25. In both cases using a hyberpola geometry for the optical transparent member 12 the spherical radii are chosen such that (1) bounces are minimized and (2) the exit angle is kept within the acceptance angle for the fiber bundle. These are found empirically by tracing numerous rays through the system or by using an optimization routine with the parameters of throughput and exit angle as functions of merit. The sperical radii are dependent on the angle of the cone or the equations defining the hyperbolic geometry.

What is claimed is:

1. An optical waveguide concentrator for combining the output radiant energy from a plurality of optoelectronic light emitting devices with minimal loss of radiant energy to the surrounding atmosphere comprising at least one solid optically transparent member having an input surface, an output surface, a sloping surface intersecting the input and output surfaces to form an acute angle, an inclined surface extending from the input surface and intersecting the sloping surface to form an acute angle to the longitudinal axis of the concentrator, with said plurality of optoelectronic light emitting devices mounted in a substantially circular array such that some or all of the light emitting devices face said inclined surface with the remainder facing said input surface and with some of said optoelectronic light emitting devices having an optical axis directed parallel to or inclined to the longitudinal axis of the concentrator.

2. An optical waveguide concentrator as defined in claim 1 wherein each optoelectronic light emitting device is selected from the group consisting of solid state or semiconductor light emitting diode(s), light emitting polymers and semiconductor lasers.

3. An optical waveguide concentrator as defined in claim 2 wherein each such optoelectronic light emitting device emits a beam of light with a divergence of less than about 15 degrees.

4. An optical waveguide concentrator as defined in claim 3 wherein said acute angle lies between 5° and 15° with respect to a plane parallel to the longitudinal axis of the concentrator.

5. An optical waveguide concentrator as defined in claim 4 wherein said optically transparent member has an external surface geometry which is conical.

6. An optical waveguide concentrator as defined in claim 5 wherein said output surface of said optically transparent member is curved.

7. An optical waveguide concentrator as defined in claim 6 wherein said output curved surface is concave in curvature.

8. An optical waveguide concentrator as defined in claim 4 wherein said optically transparent member has an external surface geometry which is hyperbolic.

9. An optical waveguide concentrator as defined in claim 8 wherein said input surface of said optically transparent member is curved.

10. An optical waveguide concentrator as defined in claim 9 wherein said curved input surface is convex in curvature.

11. An optical waveguide concentrator as defined in claim 4 wherein said solid optically transparent member further comprises a transparent section of cylindrical geometry extending from said input surface in alignment with the longitudinal axis of the transparent member.

12. An optical waveguide concentrator as defined in claim 11 further comprises at least one additional optoelectronic light emitting device with its optical axis in alignment with the longitudinal axis of the optical transparent member.

13. An optical waveguide concentrator as defined in claim 11 wherein said cylindrical section has at least one opening adapted to receive said optoelectronic light emitting device.

14. An optical waveguide concentrator as defined in claim 4 comprising at least two stages with each stage including one of said solid optically transparent members with each solid optically transparent member of each stage arranged in tandum with respect to one another and having a common longitudinal axis.

15. An optical waveguide concentrator as defined in claim 13 wherein the first stage has a circular array of at least eight LED's mounted adjacent the input surface of the solid optically transparent member of said second stage.

16. An illuminating device comprising a housing having a longitudinal axis, a waveguide concentrator having at least one solid optically transparent member with a longitudinal axis concentric to the longitudinal axis of the housing and having, in cross section, a sloping surface having a tapered angle of between 5° and 15° with respect to the longitudinal axis of the solid optically transparent member, an input and an output surface intersecting the sloping surface and lying substantially transverse to said longitudinal axis, an array of optoelectronic light emitting devices mounted around said solid optically transparent member with each optoelectronic light emitting device having an optical axis parallel to or inclined relative to said longitudinal axis and a source of power for said array of optoelectronic light emitting devices.

17. An illuminating device as defined in claim 16 further comprising control means for controlling the output from said waveguide concentrator, a light guide having one section internal of said housing in alignment with said longitudinal axis and in physical proximity to said waveguide concentrator and a curved section extending from said housing external of said device.

18. An illuminating device as defined in claim 16 wherein said array of optoelectronic light emitting devices have more than one output wavelength and further comprising switch means for selectively turning on and off the light emitting devices of said different wavelengths.

19. An illuminating device as defined in claim 16 wherein said optically transparent member has an external surface coating of a dielectric or metallic composition.

20. An optical waveguide concentrator for combining the output radiant energy from a plurality of optoelectronic light emitting devices each of which emit a beam of light with a divergence of less than about 15 degrees with minimal loss of radiant energy to the surrounding atmosphere comprising at least one solid optically transparent member the external geometry of which forms an hyperboloid having an input surface, an output surface and a sloping surface intersecting the input and output surfaces to form an acute angle of between 5° and 15° with respect to a plane parallel to the longitudinal axis of the concentrator with said plurality of optoelectronic light emitting devices mounted in a substantially circular array facing said input surface and with some of said optoelectronic light emitting devices having an optical axis directed parallel to or inclined to the longitudinal axis of the concentrator.

21. An optical waveguide concentrator as defined in claim 20 wherein said output surface of said optically transparent member is curved.

\* \* \* \* \*